United States Patent [19]

Bernstein

[11] Patent Number: 4,998,934
[45] Date of Patent: Mar. 12, 1991

[54] NEEDLE ADAPTOR FOR AN ELECTROSURGICAL TOOL

[76] Inventor: Gerald Bernstein, 6653 NE. Windermere Rd., Seattle, Wash. 98115

[21] Appl. No.: 397,160

[22] Filed: Aug. 21, 1989

[51] Int. Cl.⁵ ............................................ A61B 17/36
[52] U.S. Cl. .................................... 606/44; 128/800
[58] Field of Search ..................... 128/800; 606/41, 44

[56] References Cited

U.S. PATENT DOCUMENTS

| 2,110,735 | 3/1938 | Marton | 606/44 |
| 2,994,324 | 8/1961 | Lemos | 606/44 |
| 3,035,580 | 5/1962 | Guiorguiev | 606/44 |
| 3,152,590 | 10/1964 | Zurdo et al. | 606/44 |
| 4,751,927 | 1/1988 | Yamada | 128/800 |
| 4,785,808 | 11/1988 | Cary | 606/44 |

Primary Examiner—Max Hindenburg
Attorney, Agent, or Firm—Christensen, O'Connor, Johnson & Kindness

[57] ABSTRACT

A needle adaptor (10) for connecting a needle (20) to an electrosurgical tool (56). The adaptor (10) includes a stem 12, an integrally formed post (14) and a collar (16) press-fitted on the stem (12). An annular ridge (50) or a spiral ridge (54) formed on the interior surface (32) of the collar (16) grips the flange (42) of the needle hub (22) to firmly hold the needle (20) in place on the post (14). The stem (12) is sized and shaped to be slidably received within a cylindrical terminal (64) positioned in the nose portion (60) of the electrosurgical tool (56).

12 Claims, 1 Drawing Sheet

NEEDLE ADAPTOR FOR AN ELECTROSURGICAL TOOL

TECHNICAL FIELD

The present invention relates to electrosurgical tools and, more particularly, to a needle adaptor for coupling a metal needle to an electrosurgical tool.

BACKGROUND OF THE INVENTION

Hyfrecators and electrocautery machines are used to perform electrosurgical procedures, such as cauterization of small bleeding wounds, and telangectacia, which is the removal of vascular lesions. These machines typically include a handheld tool that has a sterilized metal tip inserted into one end. Electric current is used to heat the tip to a predetermined temperature for accomplishing the desired procedure.

There are several drawbacks to use of the metal tips. First, there is a risk that the hepatitis virus will be transmitted from patient to patient when nonsterilized metal tips are reused. As a result, after a tip is used on one patient, it should be sterilized prior to use on another patient. Sterilization has the disadvantage of requiring time and labor in the cleaning and handling of the tip. In addition, these metal tips are relatively expensive, requiring a substantial investment to build up an adequate supply to meet patient needs, which also increases the cost of medical care. Consequently, there is a need for an electrosurgical tip that is not only sterile but is relatively inexpensive and disposable, doing away with the need for sterilization.

SUMMARY OF THE INVENTION

The present invention provides a needle adaptor that permits the use of standard hypodermic needles with an electrosurgical tool. The adaptor comprises a shaft having a stem portion, which is sized and shaped to engage an electrosurgical tool, and a post portion, which is sized and shaped to receive a needle hub; and a retaining member associated with the shaft for retaining the needle hub on the shaft.

In accordance with another aspect of the present invention, the retaining member comprises a collar having means thereon for gripping the needle hub to hold the needle hub on the post portion. Preferably, the gripping means comprises internal threads formed on an interior surface of the collar wall that engage a flange projecting from the hub of the needle.

In accordance with another aspect of the present invention, the gripping means comprises internal ridges formed on an interior surface of the collar for releasably gripping a flange projecting from the needle hub.

In accordance with still yet another aspect of the present invention, the stem portion and the post portion are formed of electrically conductive material and are in electrical contact with each other.

As will be readily appreciated from the foregoing description, the needle adaptor allows any metal needle to be used with the electrosurgical tool. As a result, a physician can use a sterile, disposable needle for each patient. In addition, the same needle used for local anesthesia can be immediately used with the electrosurgical tool. Consequently, the needle adaptor of the present invention not only provides a tip at a fraction of the cost of standard tips, it also significantly reduces the risk of spreading diseases from patient to patient that can occur with standard reused, nonsterilized electrodesiccator tips.

BRIEF DESCRIPTION OF THE DRAWINGS

The foregoing and other features and advantages of the present invention will be more readily appreciated as the same becomes better understood from the detailed description when taken in conjunction with the following drawings, wherein.

DETAILED DESCRIPTION OF THE PREFERRED EMBODIMENT

Figure 1:
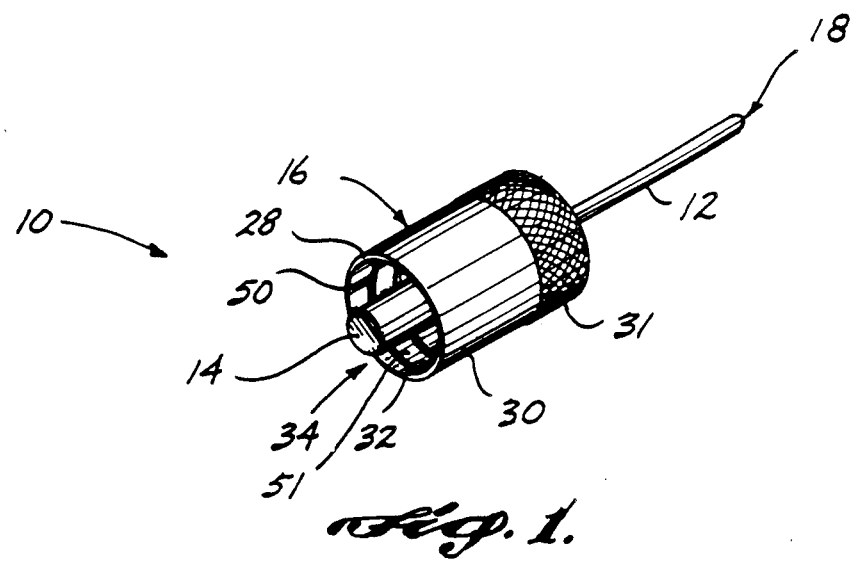
FIG. 1 is an isometric view of a needle adaptor formed in accordance with the present invention.

Referring initially to FIG. 1, the needle adaptor 10 comprises generally a stem 12, a post 14, and a collar 16 formed concentrically about the post 14. Preferably, the stem 12 and the collar 16 are formed of electrically conductive material, ideally stainless steel, and are in electrical contact with each other. The collar 16 may be slidably received on either of the stem 12 or the post 14 to rotate about the longitudinal axis thereof, but preferably the collar 16 is separately formed, as will be described in more detail hereinbelow. Similarly, the stem 12 and the post 14 may be separately constructed and attached together, but preferably they are integrally formed.

Figure 2:
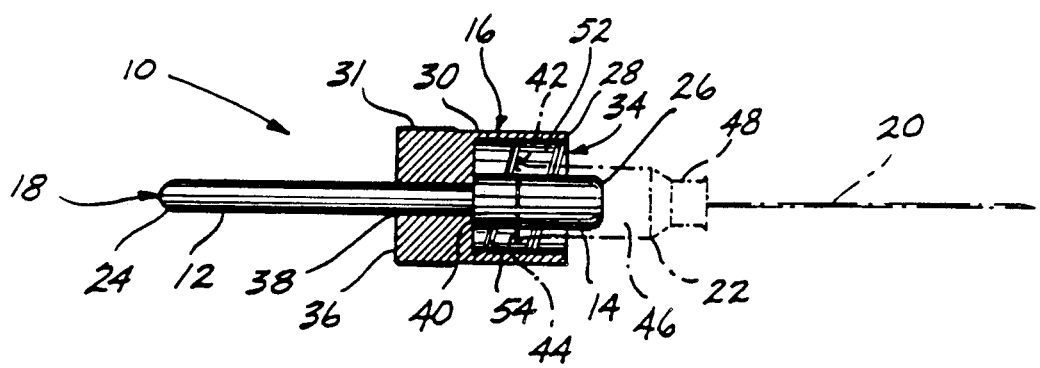
FIG. 2 is a cross-sectional side view of a needle adaptor formed in accordance with the present invention having a needle slidably received thereon.

As shown more clearly in FIG. 2, the stem 12 and the post 14 are formed from a single rod 18. The stem 12 has a diameter that is sized and shaped to be slidably received within an electrosurgical tool, as will be described in more detail below. The post 14 is sized and shaped to receive the hub 22 of a needle 20. Although the post 14 is shown having a diameter larger than the stem 12, it is to be understood that the post 14 may be constructed to have a larger or smaller diameter to accommodate a needle hub of a different size. The stem 12 has a length greater than the post 14 with a projecting end 24 that is slightly beveled to facilitate fitting of the collar 16. Similarly, the post 14 has a receiving end 26 that is beveled or rounded to facilitate insertion into the hub 22 of the needle 20.

The collar 16 is preferably constructed of stainless steel to have a cylindrical shape formed by a wall 28 having an exterior surface 30 and an interior surface 32 that defines a cavity 34. An end wall 36 closes off one side of the cavity 34. The exterior surface 30 of the collar 16 has a knurled portion 31 to facilitate gripping and twisting of the adaptor 10. An opening 38 is formed in the end wall 36 that is sized and shaped to be slidably received over the stem 12. Ideally, the opening 38 is sized to achieve a press fit over the stem 12 such that the collar 16 will not be removable. The collar 16 is placed over the stem 12 and moved toward the post 14 until the end wall 36 contacts a shoulder 40 formed between the post 14 and the stem 12. In this position, the wall 28 circumscribes the post 14.

The hub 22 of the needle 20 has a hollow interior 46 that is closed at one end by a nose 48, and has an opening 44 in the other end that is encircled by a radially projecting flange 42. The needle hub 22 is formed of metal to provide electrical and thermal conductivity with the needle 20. The needle 20 is mounted in the nose 48 of the hub 22 to extend outwardly therefrom. The interior 46 is sized and shaped to be slidably received on the post 14.

In the representative embodiment depicted in FIG. 2, a ridge 54 is spirally formed to project from the interior surface 32 of the collar 16 to define a spiral groove 52. With this construction, the ridge 54 acts as a thread, such that turning of the needle adaptor 10 about its longitudinal axis in a predetermined direction will cause the ridge 54 to engage the flange 42 and pull it into the cavity 34 of the collar 16 and hold the needle hub 22 tightly on the post 14. Alternatively, as depicted in FIG. 1, the interior surface 32 of collar 16 may be provided with a number of individual ridges 50 that form annular rings that define a set of annular grooves 51 therebetween and that provide an interference fit with flange 42 of the needle hub 22 depicted FIG. 1, the ridges 50 form individual, unconnected annular rings that provide an interference fit with the flange 42 of the needle hub 22. As such, the hub 22 will snap past the projecting ridges 50 and be retained within the grooves 51 with sufficient interference to prevent the hub 22 from unintentionally being removed from the post 14, such as by the force of gravity or with very little tension.

Figure 3:
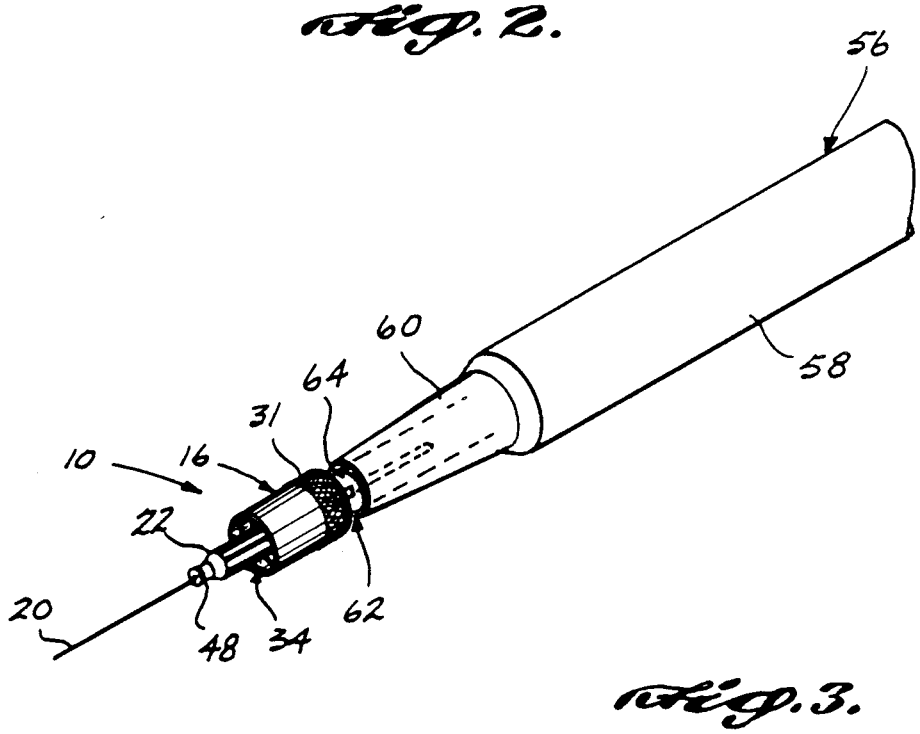
FIG. 3 is an isometric view of a needle adaptor and a needle attached to an electrosurgical tool.

The use and operation of the needle adaptor 10 will now be described in conjunction with FIG. 3. Initially, the needle adaptor 10 has the needle 20 mounted thereon by sliding the hub 22 over the post 14 and securing it in position by either snapping it in place past the ridges 50 or threading it with the ridge 54 (FIG. 2) as described above. Once the needle 20 is in place, the needle adaptor 10 is connected to an electrosurgical tool 56 by inserting the stem 12 into the receiving end 58 of the tool. Because these tools are well known in the art and are readily commercially available, they will not be described in detail here.

Briefly, the electrosurgical tool 56 has a handle portion 58 with a nose portion 60 projecting outward therefrom. The nose portion 60 has an open end 62 in which is mounted a cylindrical terminal 64. The stem 12 is slidably received within the cylindrical terminal 34 to make electrical contact with the tool 56. When electric current is provided to the cylindrical terminal 64, the needle adaptor 10 conducts the electric current and heat generated thereby to the needle 20 through the post 14 and the needle hub 22.

While a preferred embodiment of the invention has been illustrated and described herein, it is to be understood that various changes may be made without departing from the spirit and scope of the invention. For instance, the collar 16 may be rotatably mounted on the stem 12 so that the needle hub 22 may be threaded onto and off of the post 14 without requiring rotation of the rod 18. Furthermore, the interior surface 32 may be formed to have grooves below the surface 32 without having individual ridges that project from the interior surface 32. Consequently, the scope of the invention is to be limited only by the appended claims.

The embodiments of the invention in which an exclusive property or privilege is claimed are defined as follows:

1. A needle adaptor for coupling a metal needle to an electrosurgical tool, the metal needle having a metal hub with a flange formed at the end thereof and an internal axial bore formed therein, the electrosurgical tool having a receiving end into which surgical tips are inserted, the adaptor comprising:
   a stem formed of electrically conductive material, said stem being sized and shaped to be slidably received within the receiving end of the electrosurgical tool;
   a post formed of electrically conductive material and in electrical contact with said stem, said post being sized and shaped to be inserted in the bore of the hub of the needle; and
   a collar associated with said post, said collar having a cylindrical wall and means for holding the needle hub onto said post.

2. The adaptor of claim 1, wherein said stem is integrally formed with said post and said collar is slidably received on said stem with said cylindrical wall positioned concentrically around said post.

3. The adaptor of claim 2, wherein said holding means comprises one or more annular ridges formed on an inside surface of said cylindrical wall for engaging the flange on the needle hub.

4. The adaptor of claim 2, wherein said holding means comprises one or more annular grooves formed on an inside surface of said cylindrical wall for engaging the flange on the needle hub.

5. The adaptor of claim 2, wherein said holding means comprises a spiral groove formed on an interior surface of said cylindrical wall for engaging the flange on the needle hub.

6. The adaptor of claim 2, wherein said holding means comprises a spiral ridge formed on an interior surface of said cylindrical wall for engaging the flange on the needle hub.

7. The adaptor of claim 6, wherein said holding means comprises one or more annular ridges formed on an interior surface of said cylindrical wall for engaging the flange on the needle hub.

8. The adaptor of claim 6, wherein said holding means comprises one or more annular grooves formed on an inside surface of said cylindrical wall for engaging the flange on the needle hub.

9. The adaptor of claim 6, wherein said holding means comprises a spiral groove formed on an interior surface of said cylindrical wall for engaging the flange on the needle hub.

10. The adaptor of claim 6, wherein said holding means comprises a spiral ridge formed on an interior surface of said cylindrical wall for engaging the flange on the needle hub.

11. The adaptor of claim 1, wherein said stem, said post, and said collar are integrally formed with one another with said cylindrical wall positioned concentrically around said post.

12. The adaptor of claim 1, wherein said collar is rotatably mounted to said post.

* * * * *

UNITED STATES PATENT AND TRADEMARK OFFICE
CERTIFICATE OF CORRECTION

PATENT NO. : 4,998,934

DATED : March 12, 1991

INVENTOR(S) : Gerald Berstein

It is certified that error appears in the above-identified patent and that said Letters Patent is hereby corrected as shown below:

| Column | Line | Error |
|---|---|---|
| 3 | 18-21 | After "22" delete "depicted in FIG. 1, the ridges 50 form individual, unconnected annular rings that provide an interference fit with the flange 42 of the needle hub 22" and insert --.-- (period). |
| 3 | 33 | After "ridges 50" insert --(FIGURE 1)-- |

Signed and Sealed this

Twentieth Day of October, 1992

*Attest:*

DOUGLAS B. COMER

*Attesting Officer*      *Acting Commissioner of Patents and Trademarks*